(12) United States Patent
Fairbourn et al.

(10) Patent No.: US 6,540,745 B1
(45) Date of Patent: Apr. 1, 2003

(54) COATED MEDICAL DEVICES

(75) Inventors: David C. Fairbourn, Sandy, UT (US); Edward A. Loeser, Sandy, UT (US)

(73) Assignee: Aeromet Technologies, Inc., Sandy, UT (US)

( * ) Notice: Subject to any disclaimer, the term of this patent is extended or adjusted under 35 U.S.C. 154(b) by 0 days.

(21) Appl. No.: 09/846,653

(22) Filed: May 1, 2001

(51) Int. Cl.[7] ................................................ A61B 18/18
(52) U.S. Cl. .......................................... 606/45; 606/41
(58) Field of Search ............................. 606/41, 42, 45, 606/48–52, 32

(56) References Cited

U.S. PATENT DOCUMENTS

| | | |
|---|---|---|
| 3,035,583 A | 5/1962 | Hirsch et al. |
| 3,799,168 A | 3/1974 | Peters |
| 4,066,817 A | 1/1978 | De Rossi |
| 4,161,950 A | 7/1979 | Doss et al. |
| 4,314,559 A * | 2/1982 | Allen ........................ 30/140 |
| 4,333,467 A | 6/1982 | Domicone |
| 4,418,057 A | 11/1983 | Groat et al. |
| 4,481,057 A | 11/1984 | Beard |
| 4,534,347 A | 8/1985 | Taylor |
| 4,545,375 A | 10/1985 | Cline |
| 4,589,411 A | 5/1986 | Friedman |
| 4,622,966 A | 11/1986 | Beard |
| 4,657,016 A | 4/1987 | Garito et al. |
| 4,674,498 A | 6/1987 | Stasz |
| 4,677,147 A | 6/1987 | Swihart et al. |
| 4,785,807 A | 11/1988 | Blanch |
| 5,053,048 A | 10/1991 | Pinchuk |
| 5,380,320 A * | 1/1995 | Morris ........................ 606/33 |
| 5,585,186 A | 12/1996 | Scholz et al. |
| 5,607,475 A | 3/1997 | Cahalan et al. |
| 5,702,387 A * | 12/1997 | Arts et al. .................... 606/45 |
| 5,736,251 A | 4/1998 | Pinchuk |
| 5,750,197 A | 5/1998 | van Ooij et al. |
| 5,925,039 A | 7/1999 | Landingham |
| 6,054,522 A | 4/2000 | Carre et al. |
| 6,070,444 A * | 6/2000 | Lontine et al. ................. 72/46 |
| 6,106,523 A * | 8/2000 | Morris ........................ 606/41 |
| 6,241,723 B1 * | 6/2001 | Heim et al. ................... 606/32 |
| 6,329,488 B1 * | 12/2001 | Terry et al. ................ 427/2.28 |

FOREIGN PATENT DOCUMENTS

| | | |
|---|---|---|
| CA | 1282664 | 4/1991 |
| EP | 0331774 B1 | 12/1994 |
| EP | 0651005 B1 | 5/1995 |
| EP | 0775497 A2 | 9/1996 |
| EP | 0982041 A1 | 3/2000 |
| WO | WO 00/27897 | 5/2000 |
| WO | WO 00/38844 | 7/2000 |

OTHER PUBLICATIONS

Absten, Gregory T., *Practical Electrosurgery for Clinicians*, 1999 (21 pages).
*Bovie Electrosurgical Generators*, What's New in Electrosurgery, Circon Corp., website printout (5 pages).
*Electrosurgical Safety*, Education Design, Section 2, website printout (3 pages).
Malis, Jerry, *From Hot Cautery to High Tech . . . a Brief History of Electrosurgery*, Bident Inernational, website printout (2 pages).
*Precise Electrosurgery*, Utah Medical Products Inc., website printout (4 pages).
*The Edge Coated Electrodes*, Valley Lab, website printout (2 pages).

* cited by examiner

Primary Examiner—Michael Peffley
(74) Attorney, Agent, or Firm—Wood Herron & Evans LLP

(57) ABSTRACT

Medical devices, such as scalpels (10), needles (30) and electrosurgical knife tips (50), are provided with a silane coating (20) directly against the parent metal (16, 33, 63) of the tissue-contacting (15) distal ends (14, 37, 60) thereof whereby to impart advantageous non-stick and/or conductive properties thereto.

50 Claims, 2 Drawing Sheets

COATED MEDICAL DEVICES

BACKGROUND OF THE INVENTION

I. Field of the Invention

The present invention relates to medical devices, and, more particularly, to such medical devices with an advantageous coating.

II. Description of Prior Art

Medical devices are used to treat human tissue in many ways. Many such devices are elongated with one end adapted to be held, either by hand or by a mounting, with the other end being comprised of a parent metal and adapted to contact or otherwise interact with human tissue. By way of example, a needle has a proximal end adapted to be mounted to a syringe cannula for injection or withdrawal of fluids from a body, or to a length of flexible tubing such as in an IV catheter. In either case, the metal distal end is adapted to be inserted into and through human skin and blood vessels for passage of fluids therethrough. Similarly, a scalpel has a proximal end adapted to be held by a surgeon's hand in use and a distal end with a metal blade adapted to interact with tissue by cutting same, for example. One specialized type of medical instrument is an electrosurgical knife or RF scalpel which is used to cut or cauterize tissue. Typical of such instruments is that they use an elongated medical device referred to as an active electrode or tip, sometimes also referred to as a Bovie tip, to contact and cauterize the tissue. The tip is electrically conductive and cooperates with another conductor, such as a dispersive electrode (monopolar) or an adjacent electrode or tip (bipolar), to allow current flow at the site to be treated. These tips have a proximal end adapted to be mounted to the knife, with the distal end defining an active metal electrode area to cut or cauterize tissue of interest.

The various medical devices must cut into and/or slide along the tissue and so it is desirable to avoid the tendency of the distal end to stick on or to the tissue. By way of example, with the Bovie tip, a surgeon must be able to move the active electrode area along the tissue without tissue or carbonaceous remains from burnt tissue sticking thereto. Several proposals have been made to provide a non-stick surface to the active electrode area, however none are entirely satisfactory. For example, the tip may be coated with PTFE or Teflon® coating. Teflon® material is not always easy to apply and may vaporize in use exposing the patient or surgeon to certain risks. Additionally, the Teflon® coating is not a good conductor. Consequently, it has been the practice to expose the edges of the tip rather than provide the edges with the desirable nonstick coating. That, in turn, has limited the ability of the tip to conduct electricity uniformly across the surface.

Other examples are to plate the tip with platinum or coat the tip with conductive ceramic. The plating or coating process can be quite complex and costly. Indeed, platinum is itself quite costly. Relatedly, ceramics can be quite brittle, thus exposing the patient to risk of injury if pieces of ceramic chip or break off from the tip. One further proposal has been to apply a conductive silver and glass frit to the parent metal of the electrosurgical knife tip, and then to sinter the frit to form a precursor. A monofunctional silane is applied over the sintered frit, with the silane filling into the microscopic interstores formed by the frit, and with any excess wiped away so as to be certain to expose the conductive frit. The sintered frit is said to be necessary because the monofunctional silane would otherwise interfere with the conductivity of the knife tip. The requirement to first apply and sinter a silver and glass frit is undesirable.

Other medical coatings, particularly for polymeric and/or other non-metallic surfaces, have proposed to, use silane as a precursor or cross-linking agent to a different, additional coating or layer to be added over the medical device. Typical of the precursor silanes is that they are also monofunctional silanes, may be a polymer as applied, and/or may include halogens or metal in the silane composition. Those attributes combined may be useful for some medical devices, but are considered to be undesirable for application to the parent metal of medical devices. In the case of electrosurgical knife tips in particular, presence of reactive material like halogens can be deleterious in use. Moreover, the use of silane as a precursor thus requires a yet further application of a different coating material, with added costs, handling and thickness that may be undesirable for the metal, tissue-contacting end of medical devices.

There is thus a need to provide a medical device with a low cost, reliable non-stick coating for the metal, tissue-contacting distal end, and in the case of electrosurgical knife tips with desirable conductive properties on the active electrode area, but without the drawbacks associated with platinum plating, ceramic coating, Teflon® coating, or a sintered frit precursor.

SUMMARY OF THE INVENTION

The present invention provides a low cost, reliable non-stick coating for the metal, tissue-contacting distal end of medical devices, and in the case of electrosurgical knife tips also affords desired conductivity, without the drawbacks associated with platinum plating, ceramic coating, Teflon® coating, or a sintered frit precursor. To this end, and in accordance with the principles of the present invention, a medical device has a proximal end portion adapted to be held and a distal end portion comprised of a parent metal and which is adapted to contact and/or interact with tissue, with at least a selected portion or aspect or all of the distal end portion, such as the active electrode area of an electrosurgical knife tip, provided with a coating consisting essentially of a silane directly applied to the parent metal at the surface of the distal end. Alternatively, or additionally, the silane coating may be a polyfunctional silane, may be an in-situ polymerized monomeric silane (i.e., it is monomeric or uncross-linked as applied and then polymerized in-situ on the device), and may further be halogen-free (particularly where the medical device is an electrosurgical knife tip). Advantageously, the coating does not include metal in the silane as applied. Silane is inexpensive compared to platinum, and possibly even when compared to Teflon® or ceramic materials, and application as the sole coating avoids the drawbacks of applying a sintered frit precursor or application of subsequent coatings with different materials. The silane may also be readily applied in liquid form, and then easily heated to form a desired stable and non-brittle coating, without the complications typical of platinum plating or problems encountered in coating with Teflon® or ceramic materials. The resulting silane coating displays both non-stick and/or conductive properties as are desired for the metal, tissue-contacting ends of medical devices, and particularly electrosurgical knife tips.

The distal end portion of such medical device can take many shapes, including flat, cylindrical, knife edge or blade-like, ball or spherical, paddle, hook, needle, and round loops, by way of example. One common electrosurgical knife tip, known as a Bovie tip, has a cylindrical shaft at the proximal end supporting a flattened active electrode area at the distal end. The electrode area has flat surfaces which, in cross-section, may present canted flat walls. The flat surfaces join at lateral peaks or edges and the canted walls of the flat surfaces may join at peak edges. Advantageously, for Bovie tips, the silane extends over at least the flat surfaces, and may further advantageously extend over the edges as well. Thus, even the edges have a non-stick coating yet are still able to conduct as desired for proper operation of the Bovie tip. For other shapes of the active electrode area of the Bovie tip, the silane coats some or all of the active electrode area which is intended to contact or interact with the tissue.

By virtue of the foregoing, there is thus provided a low cost, reliable non-stick coating for the metal, tissue-contacting distal end of medical devices, and in the case of electrosurgical knife tips also affords desired conductivity, without the drawbacks associated with platinum plating, ceramic coating, Teflon® coating, or a sintered frit precursor. These and other objects and advantages of the present invention shall be made apparent from the accompanying drawings and the description thereof.

BRIEF DESCRIPTION OF THE DRAWINGS

The accompanying drawings (not to scale), which are incorporated in and constitute a part of this specification, illustrate embodiments of the invention and, together with the general description of the invention given above and the detailed description of the embodiments given below, serve to explain the principles of the present invention.

DETAILED DESCRIPTION OF THE DRAWINGS

Figure 1:
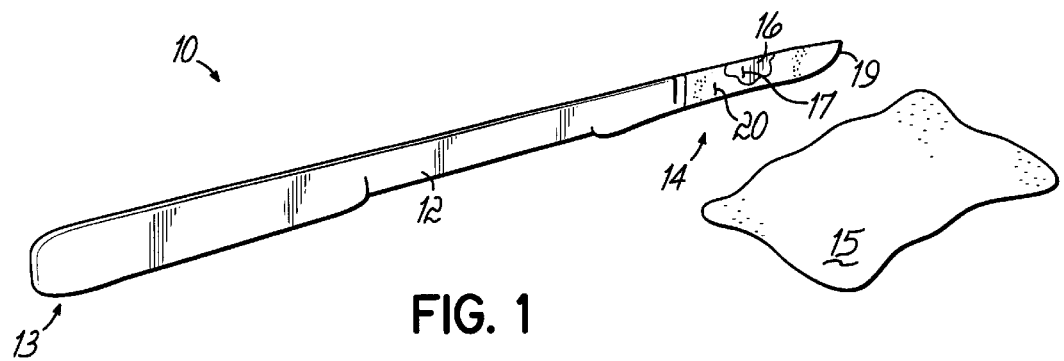
FIG. 1 is a perspective, partially cut-away view of a first exemplary medical device in the form of a scalpel with a silane coating in accordance with the principles of the present invention.

With reference to FIG. 1, there is shown in perspective view a medical device 10 such as a scalpel being an elongated metal member 12 having a proximal handle end 13 adapted to be held such as by a surgeon's hand (not shown) and a distal integral or detachable cutting end 14 adapted to contact and/or interact with tissue 15. Cutting end 14 of scalpel 10 is typically comprised of a primary or parent metal 16 such as an alloy or composite, to thus have at the surface(s) 17 thereof the parent metal 16 making up distal end 14. Distal end 14 is desirably able to glide along human tissue 15 as the knife edge 19 thereof cuts same and without unduly sticking thereto. To this end, and in accordance with the principles of the present invention, some selected portion or aspect or all of cutting end 14 is provided with a silane coating 20 which is applied directly to or otherwise against parent metal 16 at surface(s) 17 making up cutting end 14 and without an intervening carrier layer, such as a sintered frit for example, by which to support coating 20. Prior to coating, the surface(s) 17 of cutting end 14 are first advantageously polished to a smooth surface using a 600 grit abrasive, such as SiC, and then, after wiping clean, cutting end 14 is immersed in sodium hydroxide solution, 1 molar, (not shown) until a water break can be seen. A liquid solution of silane 20 is then applied, such as by spraying, dipping or painting, to the polished surface(s) 17 of cutting end 14, or those portions thereof desired to be coated. The liquid silane is then dried to form the hard coating 20. While one or more layers of coating 20 may be applied, it will be appreciated that the resultant coating applied to surface(s) 17 consists essentially of the silane (in one or more layers) without either a precursor or a subsequent coating of a different material (all not shown). Further advantageously, silane coating 20 is formed by applying an uncross-linked or monomeric liquid silane to surface(s) 17 which liquid silane is then polymerized in-situ. The silane in its liquid state may further be halogen-free and/or a polyfunctional silane.

Figure 2:
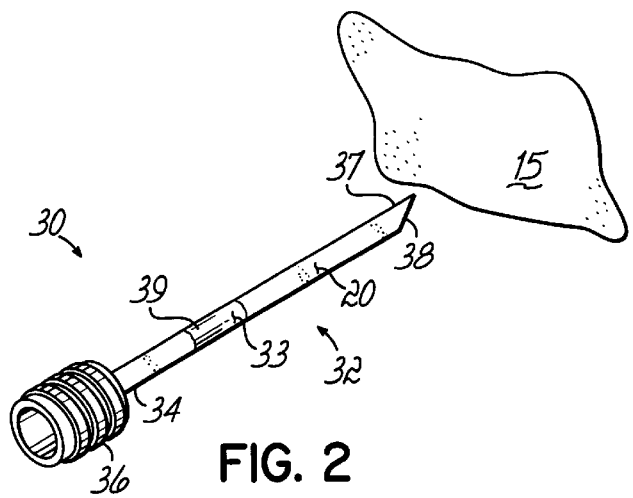
FIG. 2 is a perspective, partially cut-away view of a second exemplary medical device in the form of a needle with a silane coating in accordance with the principles of the present invention.

With reference to FIG. 2, there is shown a second exemplary medical device 30 such as a needle (shown enlarged). Needle 30 is an elongated member 32 comprised of a parent metal 33 at surface 39. Member 32 has a proximal end 34 adapted to be held such as by a syringe mount 36 or a catheter tube mount (not shown). The distal end 37 of needle 30 is sharpened as at 38 so as to puncture tissue 15 such as the skin and/or a blood vessel wall. To facilitate ease of entry thereof into the tissue 15 and/or through a sheath introducer or the like (not shown), at least a selected portion or aspect of the surface 39 of needle 30 at distal end 37, such as tip 38, if not all of needle 30, is polished and coated with silane 20 directly against the parent metal of needle 30 as above described in the case of distal end 14 of scalpel 10.

Figure 3:
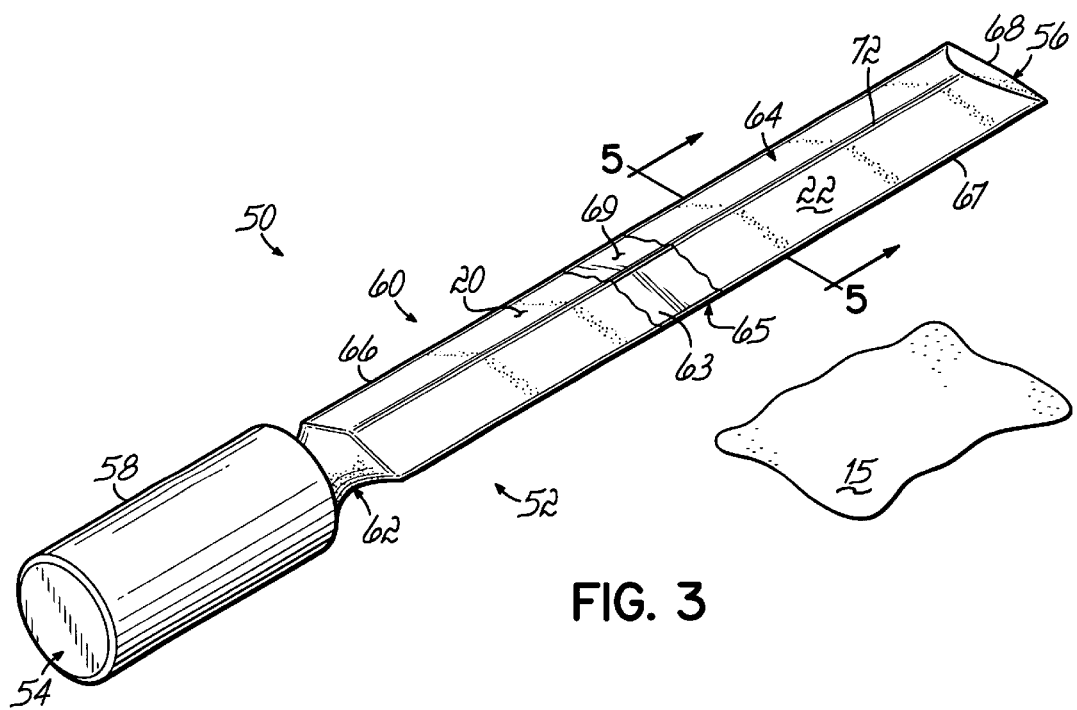
FIG. 3 is a perspective, partially cut-away view of a third exemplary medical device in the form of a first Bovie tip with a silane coating in accordance with the princples of the present invention.

With reference to FIG. 3, there is shown in perspective view a third exemplary medical device 50 such as a first electrosurgical knife tip in the form of a Bovie tip. As characteristic of many medical devices, tip 50 is an elongated metal or conductive member 52 extending between a proximal end 54, and a distal end 56. Member 52 includes a proximal portion 58 extending from proximal end 54, such as a cylindrically-shaped shaft adapted to be held such as by being coupled to the electrosurgical knife handle (not shown). Extending from distal end 56 of member 52 is a distal portion 60, such as an active electrode area which is adapted to contact human tissue 15 for cutting and/or cauterizing same. Shaft 58 and electrode area 60 are an integral unit and so may be seen to join together as at 62. Although other metals may be used, member 52 shown here is comprised of conductive parent metal 63 such as 18-8 surgical stainless steel, such that shaft 58 and electrode area 60 are electrically conductive.

Figure 5:
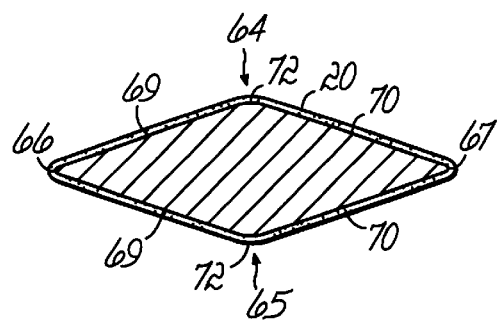
FIG. 5 is a view taken along lines 5—5 of FIG. 3.
Figure 6:
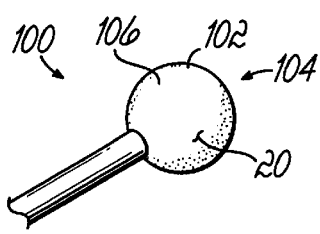
FIG. 6 is a first alternative active electrode area of a Bovie tip with a silane coating in accordance with the principles of the present invention.
Figure 7:
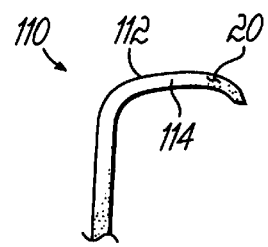
FIG. 7 is a second alternative active electrode area of a Bovie tip with a silane coating in accordance with the principles of the present invention.
Figure 8:
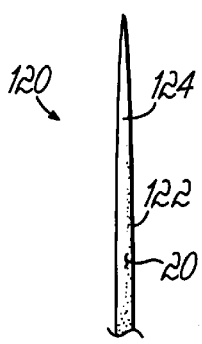
FIG. 8 is a third alternative active electrode area of a Bovie tip with a silane coating in accordance with the principles of the present invention.
Figure 9:
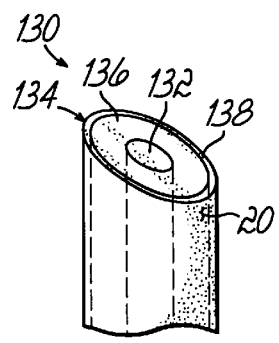
FIG. 9 is a fourth alternative active electrode area of a Bovie tip with a silane coating in accordance with the principles of the present invention.
Figure 10:
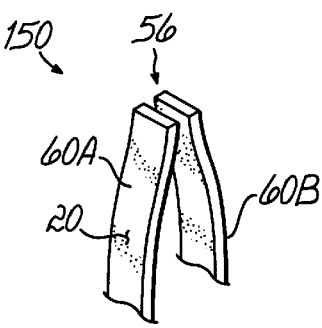
FIG. 10 is a fifth alternative active electrode area of a Bovie tip with a silane coating in accordance with the principles of the present invention.

For Bovie tips, electrode area 60 is generally characterized in that it is flattened as compared with shaft 58 so as to have an upper generally flat surface 64 and a lower generally flat surface 65 which surfaces meet at lateral edges 66, 67. Lateral edges 66, 67 may join along a front edge 68 at the distal end 56 of member 52. The flat surfaces 64 and 65 may be co-planar as in the case of a rectangular cross-section of area 60 (see FIG. 10) or may include canted flat walls 69, 70 extending from edges 66, 67, respectively, and joining along peak edges 72 to provide a diamond-shaped cross-section (FIG. 5). Either way, surfaces 64, 65 are considered generally flat in relation to the cylindrical shaft 58. Peak edges 72 of surfaces 64, 65 merge into front edge 68. Other shapes may be employed depending upon the characteristics of the medical device to be used, examples of which will be described below with reference to FIGS. 6 through 10.

Figure 4:
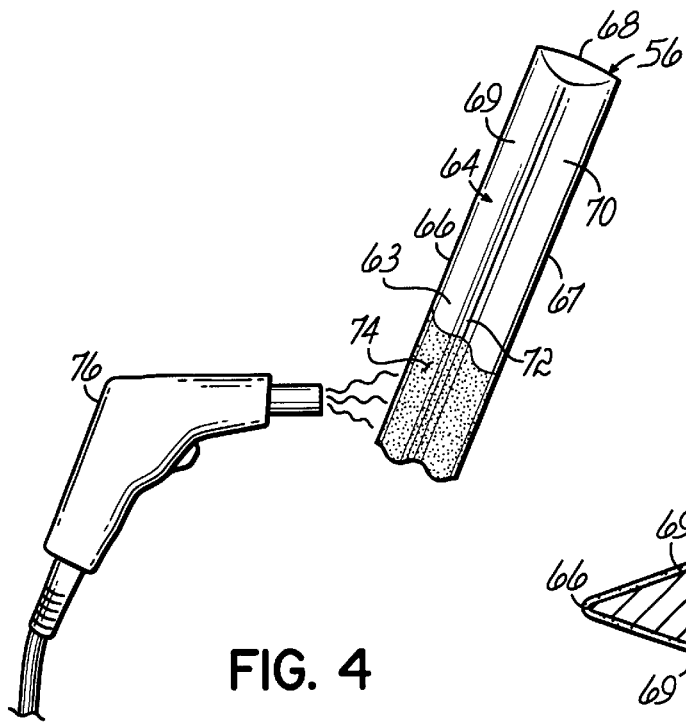
FIG. 4 is an enlarged, partially exposed view of the active electrode area of the Bovie tip of FIG. 3 showing application of liquid silane thereto.

The distal portion 60 of the medical device 50 is adapted to contact and/or interact with human tissue 15 to cut and/or cauterize same. It is desired, therefore, that portion 60 be able to glide along human tissue without unduly sticking thereto. Moreover, where the device is an electrosurgical knife tip, it is desired that the area 60 move along the tissue without buildup of tissue or carbonaceous remains caused by cauterized tissue, yet also be able to conduct electricity generally uniformly across electrode area 60 in order to properly cauterize the tissue. To this end, and in accordance with the principles of the present invention, some selected aspect or all of at least the distal portion 60, such as a portion of the electrode area of knife tip 50, is provided with a silane coating 20 (FIG. 5) applied directly to parent metal 63 of tip 50 such as at surface 64 and/or 65 and related edges 66, 67, 68 and/or 72. Prior to coating, the surfaces and edges of electrode area 60 to be coated (all or part thereof) are advantageously polished to a smooth surface using a 600 grit abrasive, such as SiC. The electrode area 60 is then immersed in sodium hydroxide solution, 1 molar, until a water break can be seen. With further reference to FIG. 4, a solution of monomeric or uncross-linked silane 74 is then applied to the polished surface(s) and/or edge(s) of those portions of distal portion 60 which are desired to be coated. The silane solution 74 is applied in its liquid state or solution form directly to extend over flat surface 64 and/or flat surface 65, for example, so as to be directly against parent metal 63. Advantageously, solution 74 is also applied to peak edge 72 and/or lateral edges 66 and 67, as well as front edge 68. Solution 74 may be readily applied in liquid form such as by spraying, dipping or painting thereon, by way of example. The silane solution 74 includes only monomeric or uncross-linked silane and so is not a polymer as applied to the medical device. Advantageously, silane solution 74 does not include a halogen or metal and may be a polyfunctional silane. The solution 74 is then dried such as with a heat gun 76 to in-situ polymerize the solution to form the hard coating 20 (FIG. 5). Liquid solution 74 may be the solution used to form coating 20 on the metal, tissue-contacting, distal ends 14 and 37 of devices 30 and 50 as well. A further layer of coating 20 may be applied if desired although it will be appreciated that the result is, in effect, that the coating applied to distal portion 60 consists essentially of silane without either a precursor or a subsequent coating of different material.

The result of coating 20 is that the coated surfaces and edges are provided with a reliable, desirably slippery, non-brittle, non-stick silane coating that is also conductive so as to provide the advantages of Teflon® coating, ceramic coating, platinum plating, and sintered frit, but without the drawbacks thereof. Additionally, the silane solution 74 may be comprised of materials that form the coating at temperatures readily obtainable without expensive or complicated equipment.

The silane suitable for use in the present invention may have mono, bis or tri functional trialkoxy silane, although polyfunctional silanes are preferred. The silane may be a bifunctional trialkoxy silyl, preferably trimethoxy or triethoxy silyl groups. Bisfunctional silane compounds are well known and two preferred for use in the present invention are bis(triethoxysilyl) ethane and bis(trimethoxysilyl) methane. In both of these compounds the bridging group between the two silane moieties is an alkyl group.

Additional commercially available polyfunctional silanes include:

1,2-Bis(tetramethyldisoloxanyl) Ethane
1,9-Bis(triethoxysilyl) Nonane
Bis(triethoxysilyl) Octane
Bis(trimethoxysilyl) Ethane
1,3-Bis(trimethylsiloxy)-1,3-Dimethyl Disiloxane
Bis(trimethylsiloxy) Ethylsilane
Bis(trimethylsiloxy) Methylsilane
AL-501 from AG Chemetall in Frankfurt Germany The silane is applied as an aqueous/alcohol solvent solution. The solvent solution will contain from about 1–2% to about 30% deionized water with the remainder being a lower alcohol such as methanol, ethanol, propanol or the like. Ethanol and methanol are preferred. The solvent is combined with the silane and generally acetic acids to establish a pH of about 4–6. The concentration of the silane compound is not relevant as long as the silane remains in solution during application. Generally, the solution will have about 1% to about 20% silane by weight.

One silane solution 74 may be formed of a monomeric variety of silane such as an organofunctional silane such as BTSE 1,2 bis(triethoxysilyl) ethane or BTSM 1,2 bis(trimethoxysilyl) methane. The silane may be dissolved in a mixture of water and acetic acid at a pH of 4, then in denatured alcohol to establish the silane solution 74. The solution has about 10 ml of distilled, de-ionized, RO water, 190 ml of denatured alcohol (mixture of ethanol and isoproponol, N.O.S.) and glacial acetic acid with approximately 10 ml of the BTSE obtained from Aldridge Chemical. Silane concentration is between about 1% and 10% and advantageously about 5%. This readily forms the more or less permanent coating 20 at temperatures readily achieved.

The silane solution 74 is applied liberally and any excess is poured off. The scalpel end 14, needle end 37 and/or knife tip 50 and solution 74 thereon are then heated such as with a heat gun 76 (FIG. 4), or even in a conventional oven (not shown) to about 250° F. for about 25 minutes, to in-situ polymerize same and form coating 20. Prior to the heating, the solution may first be allowed to dry thereon such as underneath a lamp (not shown). Heating of the solution to form coating 20 may be accomplished by heat treating scalpel 10, needle 30 or knife tip 50 with the silane solution 74 thereon. Generally, formed coating 20 will be 0.01 to 2.0 g/cm$^2$ of surface.

In use, solution 74 is applied directly to the parent metal at the polished or smooth surface of those portions or all of distal portion 14, 37 or electrode area 60 desired to be coated (and the proximal ends 14, 34 or shaft 58, if desired), and then heated to form a hard polyorganosilane coating 20. Scalpel 10 or needle 30 with silane coating 20 thereon, is then able to be used to contact and/or interact with tissue 15, and tip 50 with coating 20 thereon is then able to be used for electrosurgical procedures as desired by the surgeon (not shown), for example, all without any precursor such as sintered frit, or any further application of different coatings over silane coating 20.

As mentioned, the distal ends of medical devices may take many shapes, as exemplified by the various active electrode Bovie tips shown in FIGS. 6 through 10. To this end, a Bovie tip 100 (FIG. 6) may include a ball nose active electrode 102 at its distal end 104 and to be coated over its polished or smooth surface 106 with silane 20 in accordance with the principles of the present invention; Bovie tip 110 (FIG. 7) may include a hook end active electrode 112 coated with silane 20 on its smooth surface 114 in accordance with the principles of the present invention; Bovie tip 120 (FIG. 8) may include a needle-shaped active electrode 122 coated with silane 20 over its smooth surface 124 in accordance with the principles of the present invention; bipolar Bovie tip 130 (FIG. 9) is in the shape of a fine needle (shown greatly enlarged and not to scale) such as for eye surgery, and may include an inner metal conductor, wire or tube rod, 132 extending to its distal end 134 with a surrounding plastic insulator ring or sheath 136 insulatively spacing an outer metal shell 138 therefrom, with shell 138 and/or distal end 134 of conductor 132 smoothed and coated with silane 20 in accordance with the principles of the present invention; and bipolar Bovie tip 150 (FIG. 10) may include two blade-like or rectangular in cross-section active electrodes 60A, 60B at the distal end 156, each of which is coated with silane 20 in accordance with the principles of the present invention.

By virtue of the foregoing, there is thus provided a low cost, reliable non-stick coating for the metal, tissue-contacting distal end of medical devices, and in the case of electrosurgical knife tips the coating also affords desired conductivity, without the drawbacks associated with platinum plating, Teflon® coating, ceramic coating, or sintered frit precursor.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. For example, while the silane coating in each case is monomeric or uncross-linked as applied, and then in-situ polymerized, the coating could be applied in multiple layers of the same silane material. Also, while the silane coating as applied in its liquid form 74 advantageously has four attributes, i.e., it is a polyfunctional silane, it is not a polymer, and it has no halogen or metal, and while the final coating has a fifth attribute, i.e., it is essentially the only coating, the coating could meet fewer than all five of the attributes, as long as in any given case at least one or more of them is met. Thus, by way of example, the liquid silane could be a monofunctional silane and/or have a halogen, provided the resultant coating is essentially the only coating on the device distal end. Alternatively, and by way of further example, a halogen-free, polyfunctional silane could be applied as one of many coatings. In addition to the foregoing, while the coating consists essentially of a silane, there could be included in the coating as applied silane and other materials which are either non-functional or may be necessary for medical applications, and the coating would still be considered to consist essentially of a silane. Further, while a scalpel, needle and Bovie tip are described, other medical devices having different geometric shapes than that shown herein, with a proximal end adapted to be held and a metal distal end adapted to contact and/or interact with tissue 15 (which may be skin, bodily fluid and/or solid masses), may be coated with silane 20 to obtain the advantages of the present invention. Further, other knife tip configurations may be utilized having active electrode areas of different shapes, such as blade-like, ball or spherical, paddle, hook, round loops, needles, and/or canonization electrodes, which shapes may be advantageously coated with silane 20 to provide the advantages of the present invention. The invention in its broader aspects is, therefore, not limited to the specific details, representative apparatus and method, and illustrative examples shown and described. Accordingly, departures may be made from such details without departing from the spirit or scope of the general inventive concept.

Having described the invention, what is claimed is:

1. An electrosurgical knife tip having a proximal end adapted to be held and a distal end with an active electrode area comprised of a parent metal extending from the distal end and adapted to contact tissue, and a coating consisting essentially of a trialkoxy silane directly against the parent metal of at least a selected portion of the active electrode area.

2. The electrosurgical knife tip of claim 1, the active electrode area having a flat surface and an edge.

3. The electrosurgical knife tip of claim 2, the silane extending over the edge.

4. The electrosurgical knife tip of claim 2, the silane extending over the surface.

5. The electrosurgical knife tip of claim 4, the silane extending over the flat surface and the edge.

6. The electrosurgical knife tip of claim 1 the silane being halogen-free.

7. The electrosurgical knife tip of claim 1, the silane being a polyfunctional silane.

8. The electrosurgical knife tip of claim 1, the silane being directly against the entire active electrode area.

9. The electrosurgical knife tip of claim 1, the active electrode area having a ball nose shape.

10. The electrosurgical knife tip of claim 1, the active electrode area having a hook end.

11. The electrosurgical knife tip of claim 1, the active electrode area having a needle.

12. The electrosurgical knife tip of claim 1, the active electrode area having a metal shell insulatively separated from a metal inner rod element.

13. The electrosurgical knife tip of claim 1, the active electrode area having a pair of blades.

14. An electrosurgical knife tip having a proximal end adapted to be held and a distal end with an active electrode area comprised of a parent metal extending from the distal end and adapted to contact tissue, and a halogen-free, polyfunctional silane coating directly against the parent metal of at least a selected portion of the active electrode area.

15. The electrosurgical knife tip of claim 14, the active electrode area having a flat surface and an edge.

16. The electrosurgical knife tip of claim 15, the silane coating extending over the edge.

17. The electrosurgical knife tip of claim 15, the silane coating extending over the surface.

18. The electrosurgical knife tip of claim 17, the silane coating extending over the flat surface and the edge.

19. The electrosurgical knife tip of claim 14, the silane coating being directly against the entire active electrode area.

20. The electrosurgical knife tip of claim 14, the active electrode area having a ball nose shape.

21. The electrosurgical knife tip of claim 14, the active electrode area having a hook end.

22. The electrosurgical knife tip of claim 14, the active electrode area having a needle.

23. The electrosurgical knife tip of claim 14, the active electrode area having a metal shell insulatively separated from a metal inner rod element.

24. The electrosurgical knife tip of claim 14, the active electrode area having a pair of blades.

25. A medical device defined by an elongated member having a proximal portion adapted to be handled and a distal portion joined to the proximal portion, the distal portion comprised of a parent metal and adapted to contact human tissue, the medical device further having an in-situ polymerized monomeric trialkoxy silane coating on at least a selected aspect of the distal portion of the elongated member and directly against the parent metal thereof.

26. The medical device of claim 25 defined by a scalpel, the distal end of which defines a cutting end having a knife edge.

27. The medical device of claim 25 defined by a needle, the proximal end of which has a mounting hub and the distal end of which includes a sharpened point.

28. The medical device of claim 25, the silane coating being halogen-free.

29. The medical device of claim 25, the silane coating being a polyfunctional silane.

30. The medical device of claim 25, defined by a Bovie tip, the distal end of which has an active electrode area.

31. A medical device defined by an elongated member having a proximal portion adapted to be handled and a distal portion joined to the proximal portion, the distal portion comprised of a parent metal and adapted to contact human tissue, the medical device further having a coating consisting essentially of a trialkoxy silane on at least a selected aspect of the distal portion of the elongated member and directly against the parent metal thereof.

32. The medical device of claim 31 defined by a scalpel, the distal end of which defines a cutting end having a knife edge.

33. The medical device of claim 31 defined by a needle, the proximal end of which has a mounting hub and the distal end of which includes a sharpened point.

34. The medical device of claim 31, the silane being halogen-free.

35. The medical device of claim 31, the silane being a polyfunctional silane.

36. A medical device defined by an elongated member having a proximal portion adapted to be handled and a distal portion joined to the proximal portion, the distal portion comprised of a parent metal and adapted to contact human tissue, the medical device further having a halogen-free, polyfunctional silane coating on at least a selected aspect of the distal portion of the elongated member and directly against the parent metal thereof.

37. The medical device of claim 36 defined by a scalpel, the distal end of which defines a cutting end having a knife edge.

38. The medical device of claim 36 defined by a needle, the proximal end of which has a mounting hub and the distal end of which includes a sharpened point.

39. A method of improving an electrosurgical knife tip having an active electrode area defined by a parent metal, the method comprising applying a coating consisting essentially of a trialkoxy silane directly onto the parent metal over at least a selected portion of the active electrode area without application of any precursor thereto.

40. The method of claim 39, wherein the active electrode is first polished prior to apply the coating thereon.

41. The method of claim 40, wherein the active electrode is polished to a smooth surface using 600 grit abrasive.

42. The method of claim 39 further comprising applying the silane in a liquid state and then drying same.

43. The method of claim 42 further comprising selecting a polyfunctional silane as the liquid silane to apply.

44. The method of claim 42 further comprising selecting a halogen-free silane as the liquid silane to apply.

45. A method of improving an electrosurgical knife tip having an active electrode area defined by a parent metal, the method comprising applying only a coating consisting essentially of a trialkoxy silane directly onto the parent metal over at least a selected portion of the active electrode area.

46. A method of improving an electrosurgical knife tip having an active electrode area defined by a parent metal, the method comprising coating a polyfunctional silane directly onto the parent metal over at least a selected portion of the active electrode area.

47. A method of improving an elongated medical device having a proximal end adapted to be held and a distal end adapted to contact tissue, wherein the distal end is comprised of a parent metal, comprising applying only coating consisting essentially of trialkoxy silane directly against the parent metal of at least a selected portion of the distal end.

48. The method of claim 47, wherein the distal end is first polished prior to coating silane thereon.

49. The method of claim 48, wherein the distal end is polished to a smooth surface using 600 grit abrasive.

50. A method of improving an elongated medical device having a proximal end adapted to be held and a distal end adapted to contact tissue, wherein the distal end is comprised of a parent metal, comprising applying a polyfunctional silane coating directly against the parent metal of at least a selected portion of the distal end.

* * * * *